(12) United States Patent
Huang

(10) Patent No.: US 11,045,243 B2
(45) Date of Patent: Jun. 29, 2021

(54) SCREW PEGGING DEVICE

(71) Applicant: SHANGHAI REACH MEDICAL INSTRUMENT CO., LTD., Shanghai (CN)

(72) Inventor: Xiaomin Huang, Shanghai (CN)

(73) Assignee: SHANGHAI REACH MEDICAL INSTRUMENT CO., LTD., Shanghai (CN)

(*) Notice: Subject to any disclaimer, the term of this patent is extended or adjusted under 35 U.S.C. 154(b) by 3 days.

(21) Appl. No.: 16/626,882

(22) PCT Filed: Jan. 29, 2019

(86) PCT No.: PCT/CN2019/073674
§ 371 (c)(1),
(2) Date: Dec. 27, 2019

(87) PCT Pub. No.: WO2020/048088
PCT Pub. Date: Mar. 12, 2020

(65) Prior Publication Data
US 2020/0367954 A1    Nov. 26, 2020

(30) Foreign Application Priority Data
Sep. 7, 2018   (CN) .......................... 201811045630.5

(51) Int. Cl.
*A61B 17/88*     (2006.01)
*A61B 17/86*     (2006.01)

(52) U.S. Cl.
CPC .............................. *A61B 17/8886* (2013.01)

(58) Field of Classification Search
CPC ... B25B 23/0035; B25G 3/18; A61B 17/8886; A61B 17/8875; A61B 17/8891; A61B 17/8888
(Continued)

(56) References Cited

U.S. PATENT DOCUMENTS

| | | | |
|---|---|---|---|
| 7,666,189 B2 * | 2/2010 | Gerber | A61B 17/7076 606/104 |
| 7,909,830 B2 * | 3/2011 | Frigg | A61B 17/7083 606/86 A |

(Continued)

FOREIGN PATENT DOCUMENTS

| | | |
|---|---|---|
| CN | 101138515 | 3/2008 |
| CN | 104688326 | 6/2015 |

(Continued)

OTHER PUBLICATIONS

International Search Report in PCT/CN2019/073674 issued by ISA, dated May 31, 2019.

(Continued)

*Primary Examiner* — Jessica Weiss
(74) *Attorney, Agent, or Firm* — Zhu Lehnhoff LLP

(57) ABSTRACT

The invention provides a screw pegging device. The screw pegging device comprises a holding handle, a handle rod, a sleeve and a screw part, wherein the sleeve is provided with a perforative cavity, and clamping grooves are arranged at two ends of the cavity; a groove opening running through the cavity is arranged in the side wall of the sleeve, a limiting clamping part is arranged in the groove opening, one end of the limiting clamping part is connected with the groove opening, and the other end of the limiting clamping part is (Continued)

provided with a convex clamping edge; the screw part is a long rod, one end of the long rod is provided with a screw head, a first clamping part is arranged at the joint of the long rod and the screw head, and an annular groove edge is arranged on the side wall of the long rod; and the holding handle sleeves one end of the handle rod, the other end of the handle rod is inserted and clamped in a third clamping groove of the sleeve, an axial insertion hole is formed in the handle rod, the long rod runs through the cavity and is inserted and embedded in the insertion hole, a fourth clamping groove is in clamping connection with the first clamping part, and the convex clamping edge is embedded and clamped in the annular groove edge. In the screw pegging device, the firm connecting is guaranteed by utilizing the clamping groove structure, the screw part long rod extends into the handle rod, then the strength of the joint of the handle rod and the screw part is enhanced, meanwhile, through the limiting clamping part, the axial limiting fixing is realized between the sleeve and screw part, and the disassembly is convenient.

4 Claims, 2 Drawing Sheets

(58) Field of Classification Search
USPC ........ 604/104; 81/177.85; 606/104, 300–321
See application file for complete search history.

(56) References Cited

U.S. PATENT DOCUMENTS

| 10,004,544 | B2 | 6/2018 | Arnold et al. | |
| 10,888,356 | B2* | 1/2021 | Beyer | A61B 17/708 |
| | | | | 606/104 |
| 2007/0078460 | A1* | 4/2007 | Frigg | A61B 17/7002 |
| | | | | 606/86 A |
| 2012/0150237 | A1* | 6/2012 | Combrowski | A61B 17/8615 |
| | | | | 606/301 |
| 2016/0338737 | A1* | 11/2016 | Sicvol | A61B 17/7037 |
| | | | | 606/104 |
| 2017/0348029 | A1* | 12/2017 | Asaad | A61B 17/7091 |
| | | | | 606/104 |

FOREIGN PATENT DOCUMENTS

| CN | 204723167 | 10/2015 |
| CN | 106137375 | 11/2016 |
| CN | 106901825 | 6/2017 |
| CN | 109247982 | 1/2019 |

OTHER PUBLICATIONS

Written Opinion of the International Search Report in PCT/CN2019/073674, issued by ISA, dated May 31, 2019.

* cited by examiner

SCREW PEGGING DEVICE

TECHNICAL FIELD

The invention belongs to the field of the medical device, and in particular relates to a screw pegging device.

BACKGROUND

At the beginning of the spinal operation, it is necessary to fix the spine for easy stretch and separation of spine. Common screws knocked in the spine are often connected with the holding handle through screw fastening or clamp, wherein, the screwed screw cannot be directly removed with the holding handle, and the swirl removal loses time during operation, bad for operation implementation. However, the clamped screw and the holding handle cannot ensure screw with screw knocked in the spine.

SUMMARY OF THE INVENTION

The invention aims to provide a screw pegging device, which is easy for removal and avoids rotation or skewing of screw to be screwed into the spine.

For this purpose, the invention puts forward a screw pegging device, comprising a holding handle, a handle rod, a sleeve and a screw, wherein:

The sleeve has a through cavity, and a third clamping groove and a fourth clamping groove are arranged inside both ends of the cavity respectively; a groove opening through the cavity is arranged on the side wall of the sleeve, a limiting clamping part paralleled to the side wall surface is arranged in the groove opening, one end of the limiting clamping part is connected with the side wall of the groove opening, and a convex clamping edge over against the cavity is arranged on the other end;

The screw has a cylinder-shaped long rod, wherein, a screw shaft is arranged on one end of the long rod, a first snap-fit portion is arranged between the long rod and the screw shaft, and an annular slot edge is arranged on a side wall of the long rod;

One end of the handle rod covers the holding handle, and the other end is inserted in the third clamping groove of the sleeve, an axial insertion hole is arranged on one end connected between the handle rod and the sleeve, and the insertion hole is through-connected with the cavity of the sleeve; the long rod passes through the cavity and is inserted in the insertion hole, the fourth clamping groove is snap-fitted in with the first snap-fit portion, and the convex clamping edge is embedded in the annular slot edge.

Further, in the screw pegging device, a first clamping groove and a second clamping groove are arranged on the side wall of both ends of the handle rod respectively, the handle rod covers the holding handle through the first clamping groove, and a second snap-fit portion that is snap-fitted in with the second clamping groove is arranged in the third clamping groove.

Further, in the screw pegging device, the diameters of the third and the fourth clamping grooves are larger than the diameter of the cavity.

Further, in the screw pegging device, the first snap-fit portion is a polygonal prism.

Further, in the screw pegging device, a protruding annular edge is arranged on one end connected between the first snap-fit portion and the screw shaft head, the annular edge is clamped on the end surface of the sleeve, and the diameter of the annular edge is larger than that of the fourth clamping groove.

Further, in the screw pegging device, several corrugations are arranged on the side wall of the long rod.

Further, in the screw pegging device, the diameter of one end connected between the holding handle and the handle rod is less than that of the other end, and several slots are arranged on the holding handle.

Compared with the prior art, the invention has the advantage that it ensures secure connection by means of multiple clamping groove structures, the screw long rod is inserted in the handle rod, strengthening the connection between the handle rod and the screw, and the sleeve and the screw are fixed axially through the limiting clamping part for easy removal.

Figure 1:
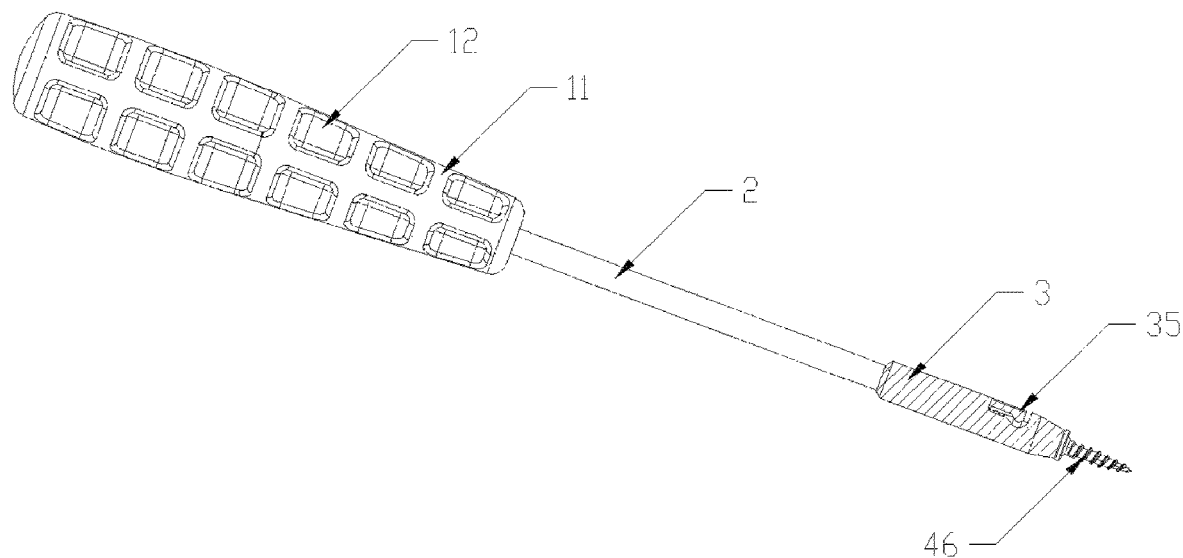
FIG. 1 is a structure diagram for the screw pegging device in the invention.
Figure 2:
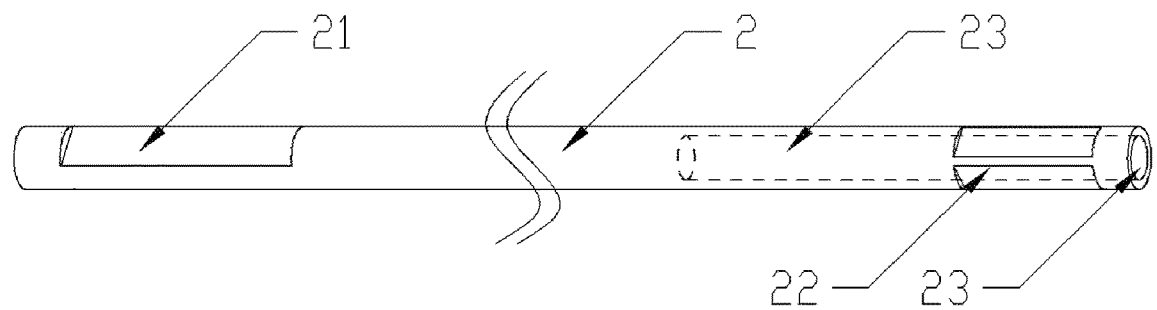
FIG. 2 is a structure diagram for the handle rod in the invention.
Figure 3:
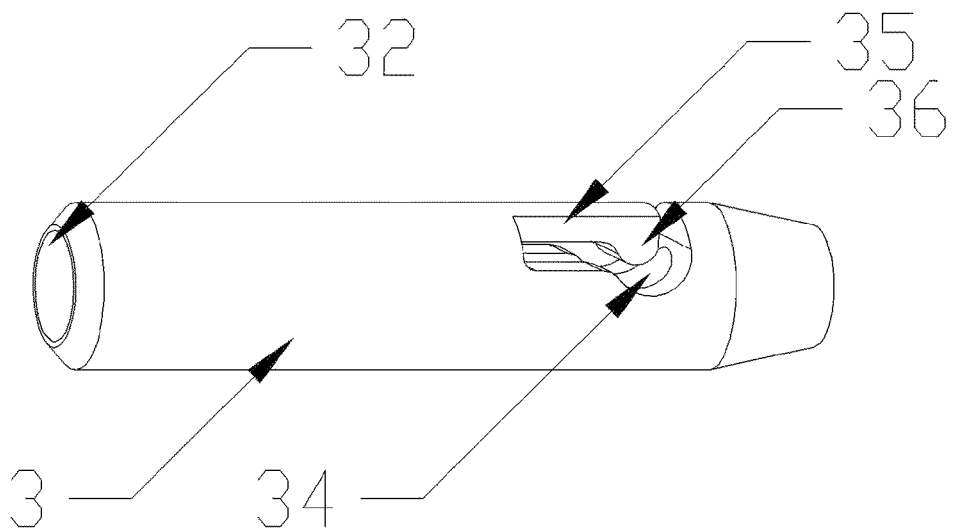
FIG. 3 is a structure diagram for the sleeve in the invention.
Figure 4:
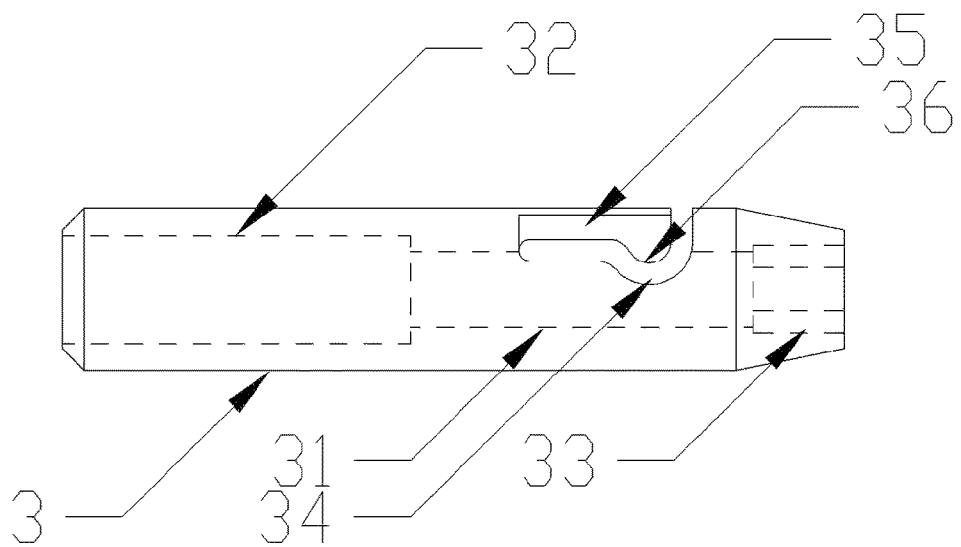
FIG. 4 is a sectional structure diagram of FIG. 3.
Figure 5:
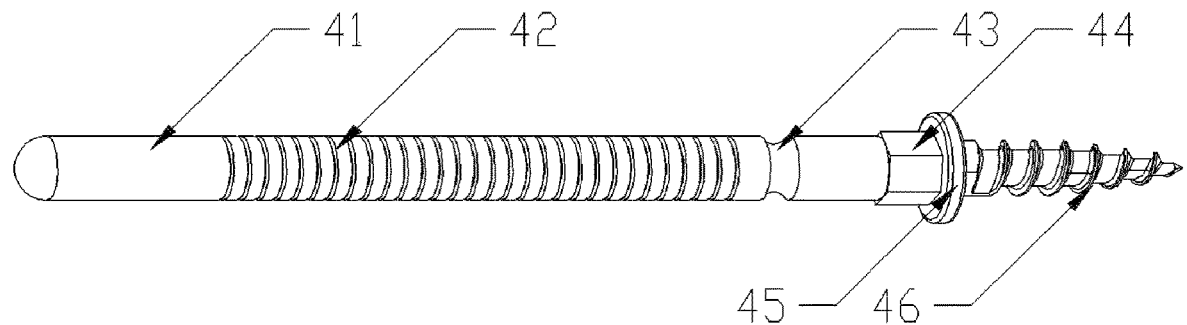
FIG. 5 is a structure diagram for the screw in the invention.

In the figure: holding handle—11; slot—12, handle rod—2; first clamping groove—21; second clamping groove—22; insertion hole—23; sleeve—3; cavity—31; third clamping groove—32; fourth clamping groove—33; groove opening—34; limiting clamping part—35; convex clamping edge—36; long rod—41; corrugation—42; annular slot edge—43; first snap-fit portion—44; annular edge—45; screw shaft head—46.

DETAILED DESCRIPTION OF THE PREFERRED EMBODIMENTS

A detailed description of the screw pegging device of the invention is given below in combination with the schematic diagram, showing the preferred embodiment of the invention. It should be appreciated that those skilled in the art can modify the invention described herein while still achieving the advantageous effects of the invention. Therefore, it should be appreciated that the following description is widely known by those skilled in the art and not intended to limit the invention.

For clarity, all characteristics of the actual embodiments are not described. In the following description, the known function and structure are not described in detail, because they will confuse the invention for unnecessary details. It should consider that lots of implementation details must be made to realize the specific objective of developer in the development of any actual embodiments, e.g., change from an embodiment to another embodiment according to the restrictions related to the system or business. Besides, it should consider that such development may be complex and time-consuming, but it is a routine work only for those skilled in the art.

In the description of the invention, it is necessary to describe that for nouns of locality, such as "center", "lateral", "longitudinal", "length", "width", "thickness", "upper", "lower", "front", "rear", "left", "right", "vertical", "horizontal", "top", "bottom", "internal", "external", "clockwise" and "anticlockwise", the relationship between such indication localities and positions is a locality or position relationship shown based on drawings, which aims to describe the utility model and simplify description only, rather than indicate or suggest that the indicated device or component must have a specific orientation and be structured and operated in specific orientation, cannot be understood as limit to specific scope of protection of the utility model.

Besides, if such terms as "first" and "second" are used to describe the purpose only, they cannot be understood as indicating or suggesting the relative importance or implying the quantity of technical features. Therefore, the feature limited to "first" and "second" can express or imply including one or more features. In the description of the invention, the implication of "at least" is one or more, unless otherwise limited.

In the invention, unless otherwise specified and limited, the terms such as "assembly", "joint" and "connection" should be understood generally, e.g., it can be fixed connection or dismountable connection or integral connection; it can also be mechanical connection; it can be direct connection or connection through intermediation or internal connection by two components. For common those skilled in the art, they can understand the specific implication of the above terms in the utility model according to the specific circumstances.

In the invention, unless otherwise specified and limited, the first feature "above" or "below" the second feature can include direct contact between the first and second features and can also include contact of other features between them rather than direct contact. Moreover, the first feature "above", "under" and "on" the second feature includes that the first feature is right above or inclined above the second feature, or represents that the horizontal height of the first feature is higher than the second feature only. The first feature "above", "under" and "below" the second feature includes that the first feature is right under or inclined under the second feature, or represents that the horizontal height of the first feature is lower than the second feature only.

In the following paragraph, the invention is described specifically in the example mode with reference to the drawings. According to the following description, the advantages and characteristics of the invention will be clearer. It is necessary to describe that all drawings use very simplified form and very accurate ratio, used to conveniently and clearly supplement the purpose of the embodiments of the invention only.

As shown in FIG. 1, the invention puts forward a screw pegging device, comprising a holding handle, a handle rod, a sleeve and a screw.

Specifically, the sleeve has a through cavity, and a third clamping groove and a fourth clamping groove are arranged inside both ends of the cavity respectively; a groove opening through the cavity is arranged on the side wall of the sleeve, a limiting clamping part paralleled to the side wall surface is arranged in the groove opening, one end of the limiting clamping part is connected with the side wall of the groove opening, and a convex clamping edge over against the cavity is arranged on the other end. The diameters of the third and the fourth clamping grooves are larger than the diameter of the cavity.

The screw has a cylinder-shaped long rod, wherein, a screw shaft is arranged on one end of the long rod, a first snap-fit portion is arranged between the long rod and the screw shaft, and an annular slot edge is arranged on the side wall of the long rod; a protruding annular edge is arranged on one end connected between the first snap-fit portion and the screw shaft, the annular edge is clamped on the end surface of the sleeve, and the diameter of the annular edge is larger than that of the fourth clamping groove. Several corrugations are arranged on the side wall of the long rod, strengthening the strength of the long rod and avoiding bending.

A first clamping groove and a second clamping groove are arranged on the side wall of both ends of the handle rod respectively; the handle rod covers the holding handle through the first clamping groove, and the other end is inserted in the third clamping groove of the sleeve; a second snap-fit portion that is snap-fitted in with the second clamping groove is arranged in the third clamping groove; both the first and second clamping grooves comprise multiple grooves, which can ensure secure connection between the handle rod with the sleeve and the holding handle, can rotate synchronously and axially, and would not loose due to force in rotation direction. An axial insertion hole is arranged on one end connected between the handle rod and the sleeve, and the insertion hole is through-connected with the cavity of the sleeve; the long rod passes through the cavity and is inserted in the insertion hole, the fourth clamping groove is snap-fitted in with the first snap-fit portion, and the first snap-fit portion is a polygonal prism, ensuring the sleeve drives the screw synchronously. The screw is inserted in the cavity of the sleeve, the side wall of the long rod extrudes the convex clamping edge outside until the convex clamping edge is embedded in the annular slot edge so that the long rod cannot be moved easily, and the sleeve and the screw are snap-fitted and fixed.

Besides, the diameter of one end connected between the holding handle and the handle rod is less than that of the other end, and many slots are arranged on the holding handle for easy hold or snap-fitting with machines.

In conclusion, in the embodiment, the screw pegging device ensures secure connection by means of multiple clamping groove structures, the screw long rod is inserted in the handle rod, strengthening the connection between the handle rod and the screw, and the sleeve and the screw are fixed axially through the limiting clamping part for easy removal.

The description above is the preferred embodiment of the invention only, and has no limit to the invention. The changes in any form, such as equivalent replacements or modifications, made to the technical solution and contents disclosed in the invention by those skilled in the art without departing from the scope of the technical solution of the invention belong to the contents without departing from the technical solution of the invention, and are still within the scope of protection of the invention.

The invention claimed is:

1. A screw pegging system, comprising: a holding handle, a handle rod, a sleeve and a screw,
   wherein the sleeve has a through cavity, a third clamping groove and a fourth clamping groove, wherein the third clamping groove and the fourth clamping groove are arranged inside opposite ends of the through cavity respectively; a groove opening through the through cavity arranged on a side wall of the sleeve, a limiting clamping part extending parallel to a side wall surface within the groove opening, wherein one end of the limiting clamping part is connected with a side wall of the groove opening, and wherein the other end of the limiting clamping part comprises a convex clamping edge extending within the groove opening;
   wherein the screw has a cylindrical long rod, a screw shaft arranged on one end of the long rod, a first snap-fit portion arranged between the long rod and the screw shaft, and an annular slot edge arranged on a side wall of the long rod;

wherein one end of the handle rod is attached to the holding handle and the other end of the handle rod is inserted into the third clamping groove of the sleeve, wherein an axial insertion hole is arranged on the end of the handle rod that is attached to the sleeve, and wherein the axial insertion hole is connected with the through cavity of the sleeve;

wherein the long rod of the screw is configured to be passed through the through cavity and inserted in the insertion hole, wherein the first snap-fit portion is snap-fitted into the fourth clamping groove, and wherein the convex clamping edge is embedded in the annular slot edge; and wherein a first clamping groove is arranged on the end of the handle rod attached to the holding handle and a second clamping groove is arranged on the other end of the handle rod, inserted into the third clamping groove of the sleeve, respectively, wherein the handle rod is attached to the holding handle by the first clamping groove, and wherein a second snap-fit portion that is snap-fitted into the second clamping groove is arranged in the third clamping groove.

2. A screw pegging system, comprising: a holding handle, a handle rod, a sleeve and a screw, wherein the sleeve has a through cavity, a third clamping groove and a fourth clamping groove, wherein the third clamping groove and the fourth clamping groove are arranged inside opposite ends of the through cavity respectively; a groove opening through the through cavity, a limiting clamping part extending parallel to a side wall surface within the groove opening, wherein one end of the limiting clamping part is connected with a side wall of the groove opening, and wherein the other end of the limiting clamping part comprises a convex clamping edge extending within the groove opening;

wherein the screw has a cylindrical long rod, a screw shaft arranged on one end of the long rod, a first snap-fit portion arranged between the long rod and the screw shaft, and an annular slot edge arranged on a side wall of the long rod;

wherein one end of the handle rod is attached to the holding handle and the other end of the handle rod is inserted into the third clamping groove of the sleeve, wherein an axial insertion hole is arranged on the end of the handle rod that is attached to the sleeve, and wherein the axial insertion hole is connected with the through cavity of the sleeve;

wherein the long rod of the screw is configured to be passed through the through cavity and inserted in the insertion hole, wherein the first snap-fit portion is snap-fitted into the fourth clamping groove, and wherein the convex clamping edge is embedded in the annular slot edge; and wherein each diameter of the third and the fourth clamping grooves of the sleeve are larger than a diameter of the through cavity.

3. The screw pegging device according to claim 2, wherein the first snap-fit portion is a polygonal prism.

4. A screw pegging system, comprising: a holding handle, a handle rod, a sleeve and a screw, wherein the sleeve has a through cavity, a third clamping groove and a fourth clamping groove, wherein the third clamping groove and the fourth clamping groove are arranged inside opposite ends of the through cavity respectively; a groove opening through the through cavity arranged on a side wall of the sleeve, a limiting clamping part extending parallel to a side wall surface within the groove opening, wherein one end of the limiting clamping part is connected with a side wall of the groove opening, and wherein the other end of the limiting clamping part comprises a convex clamping edge extending within the groove opening;

wherein the screw has a cylindrical long rod, a screw shaft arranged on one end of the long rod, a first snap-fit portion arranged between the long rod and the screw shaft, and an annular slot edge arranged on a side wall of the long rod;

wherein one end of the handle rod is attached to the holding handle and the other end of the handle rod is inserted into the third clamping groove of the sleeve, wherein an axial insertion hole is arranged on the end of the handle rod that is attached to the sleeve, and wherein the axial insertion hole is connected with the through cavity of the sleeve;

wherein the long rod of the screw is configured to be passed through the through cavity and inserted in the insertion hole, wherein the first snap-fit portion is snap-fitted into the fourth clamping groove, and wherein the convex clamping edge is embedded in the annular slot edge; and wherein the holding handle comprises a plurality of slots and wherein a diameter of one end of the holding handle that is attached to the handle rod is smaller than a diameter of the other end of the holding handle.

* * * * *